United States Patent [19]

Reuther et al.

[11] Patent Number: 5,216,010
[45] Date of Patent: Jun. 1, 1993

[54] BIOCIDAL N-THIOCYANATOMETHOXYAZAHETEROCYCLES

[75] Inventors: Wolfgang Reuther, Heidelberg; Ulf Baus, Dossenheim; Gisela Lorenz, Neustadt, all of Fed. Rep. of Germany

[73] Assignee: BASF Aktiengesellschaft, Ludwigshafen, Fed. Rep. of Germany

[21] Appl. No.: 692,728

[22] Filed: Apr. 29, 1991

[30] Foreign Application Priority Data

Apr. 30, 1990 [DE] Fed. Rep. of Germany ....... 4013874

[51] Int. Cl.⁵ .................... A01N 43/56; C07D 231/12
[52] U.S. Cl. .................... 514/407; 514/184; 548/101; 548/375.1
[58] Field of Search ............... 514/407, 184; 548/375, 548/101, 375.1

[56] References Cited

U.S. PATENT DOCUMENTS 2,888,462  5/1959  Cannon .............................. 548/375
4,764,527  8/1988  Wagner et al. ..................... 514/407

Primary Examiner—Patricia L. Morris
Attorney, Agent, or Firm—Oblon, Spivak, McClelland, Maier & Neustadt

[57] ABSTRACT

N-Thiocyanatomethoxyazaheterocycles of the general formula I $$NCS-CH_2-O-Het$$

(where Het is pyrazolyl, imidazolyl or triazolyl, each of which may be substituted, or is indazolyl, benzoimidazolyl or benzotriazolyl, where each of the fused benzene rings may furthermore be substituted, and the salts and metal complexes thereof, with the exception of 1-[(thiocyanato)methoxy]-pyrazole, and biocides containing them.

3 Claims, No Drawings

BIOCIDAL N-THIOCYANATOMETHOXYAZAHETEROCYCLES

The present invention relates to novel N-thiocyanatomethoxyazaheterocycles of the formula I NCS—CH$_2$—O—Het where Het is
pyrazol-1-yl, imidazol-1-yl, 1,2,3-triazol-1-yl or 1,2,4-triazol-1-yl, where these substituents may furthermore carry on each carbon atom a C$_1$–C$_4$-alkyl group or phenyl which may be monosubstituted to trisubstituted by halogen, C$_1$–C$_4$-alkyl or C$_1$–C$_4$-alkoxy and-/or partially or completely halogenated C$_1$–C$_4$-alkyl, or indazol-1-yl, benzimidazol-1-yl or benzotriazol-1-yl, where the fused benzene rings of these substituents may furthermore each carry up to three of the following radicals: halogen, C$_1$–C$_4$-alkyl, C$_1$–C$_4$-alkoxy or partially or completely halogenated C$_1$–C$_4$-alkyl, and the plant-tolerated salts and metal complexes thereof, with the exception of 1-[(thio- cyanato)-methoxy]-pyrazole.

The present invention furthermore relates to processes for the preparation of these compounds, their use as biocides and biocides which contain these compounds as active substances.

DE-A 36 20 579 discloses N-thiocyanatomethoxypyrazole and derivatives of this compound which are substituted by halogen in the pyrazole ring for controlling microorganisms, such as bacteria, fungi and algae.

However, the actions of these compounds against microorganisms are satisfactory only to a limited extent, particularly in the case of low application rates and concentrations.

It is an object of the present invention to provide novel biocidal N-thiocyanatomethoxyazaheterocycles having an improved action.

We have found that this object is achieved by the N-thiocyanatomethoxyazaheterocycles of the formula I which have been defined at the outset.

In the novel compounds I, the azaheterocyclic structure has the following specific meanings
pyrazol-1-yl, imidazol-1-yl, 1,2,3-triazol-1-yl or 1,2,4-triazol-1-yl, where these substituents may furthermore carry on each carbon atom one of the following radicals: straight-chain or branched C$_1$–C$_4$-alkyl, such as methyl, ethyl or tert-butyl, preferably methyl, phenyl which may carry up to three of the following radicals: halogen, preferably fluorine, chlorine or bromine, straight-chain or branched C$_1$–C$_4$-alkyl, such as methyl, ethyl or tert-butyl, partially or completely halogenated C$_1$–C$_4$-alkyl, such as trifluoromethyl, trichloromethyl, pentafluoroethyl or 2-chloro-1,1,2-trifluoroethyl, and/or straight-chain or branched C$_1$–C$_4$-alkoxy, preferably methoxy or ethoxy; in particular phenyl, halophenyl, such as 2-fluorophenyl, 3-fluorophenyl, 4-fluorophenyl, 2-chlorophenyl, 3-chlorophenyl, 4-chlorophenyl, 2-bromophenyl, 3-bromophenyl or 4-bromophenyl, dihalophenyl, such as 2,3-dichlorophenyl, 2,4-dichlorophenyl, 2,5-dichlorophenyl, 2,6-dichlorophenyl, 2-chloro-4-fluorophenyl or 2-chloro-6-fluorophenyl, alkylphenyl, such as 4-methylphenyl, 4-ethylphenyl, 4-isopropylphenyl or 4-tert-butylphenyl, haloalkoxyphenyl, such as 2-chloro-6-methoxyphenyl, alkoxyphenyl, such as 2-methoxyphenyl, 3-methoxyphenyl, 4-methoxyphenyl or 4-ethoxyphenyl, or dialkoxyphenyl, such as 2,4-dimethoxyphenyl or 3,4-dimethoxyphenyl;
indazol-1-yl, benzimidazol-1-yl or benzotriazol-1-yl, where the fused benzene rings of these substituents may furthermore each carry up to three of the following radicals: halogen, preferably fluorine, chlorine or bromine, straight-chain or branched C$_1$–C$_4$-alkyl, such as methyl, ethyl, propyl, isopropyl, butyl or tert-butyl, preferably methyl,
straight-chain or branched C$_1$–C$_4$-alkoxy, such as methoxy, ethoxy, propoxy or tert-butoxy, preferably methoxy, or partially or completely halogenated C$_1$–C$_4$-alkyl, preferably trifluoromethyl, trichloromethyl, pentafluoroethyl or 2-chloro-1,1,2-trifluoromethoxy.

Preferred compounds I are 1-thiocyanatomethoxypyrazole and those derivatives of this compound which are monosubstituted or disubstituted by methyl in the pyrazole ring, particularly preferably 1-thiocyanatomethoxy-1,2,4-triazole.

The N-thiocyanatomethoxyazaheterocycles I are obtainable in various ways, preferably from compounds of the formula IIa HO-Het  IIa by the following methods:
a) Reaction with methylene bisthiocyanate

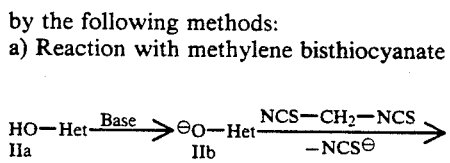

The synthesis disclosed in DE-A 317 912 is generally carried out in inert solvents, for example ethers, such as diethylether, tetrahydrofuran or diethylene glycol dimethyl ether, or aromatic hydrocarbons, such as toluene.

In principle, however, solvent mixtures of water and an inert, water-miscible or immiscible organic solvent are also suitable.

In the first reaction step, the heteroaromatic IIa is converted into its alcoholate IIb by a known method with a basic alkali metal compound or alkaline earth metal compound, for example an alkali metal hydroxide, alkali metal hydride or alkali metal carbonate. Preferred bases are lithium, sodium, potassium and magnesium compounds, such as butyllithium, sodium hydroxide, sodium hydride and sodium carbonate.

The alcoholate and the methylene bisthiocyanate are usually used in equimolar amounts or with up to about 10% excess of one or other component.

In general, the reaction temperature is from 0° to 100° C., preferably from 10° to 70° C., in particular from 20° to 25° C. (room temperature).

As the reaction is not pressure-dependent, it is advisable to employ atmospheric pressure. b) Reaction with chloromethyl thiocyanate

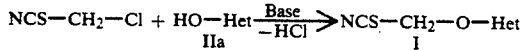

The synthesis disclosed in DE-A 36 20 579 is carried out as a rule in inert solvents, for example aromatic and aliphatic hydrocarbons or chlorohydrocarbons, such as toluene or methylene chloride, ethers, such as diethyl ether, tetrahydrofuran or diethylene glycol dimethyl ether, alcohols, such as tert-butanol, ketones, such as acetone, nitriles, such as acetonitrile, or amides, such as N,N-dimethylformamide.

Examples of suitable bases are tertiary amines, pyridine, alkali metal carbonates, alkali metal hydroxides, alkali metal hydrides and alkali metal alcoholates.

In general, the temperature is from −60° to 180° C., preferably from 20° to 80° C.

Regarding the stoichiometric ratios and the pressure, the statements made for method a) are applicable.

The reaction can also be carried out in a two-phase system under phase transfer catalysis. A mixture of a chlorohydrocarbon, such as methylene chloride, an aqueous alkali, for example sodium hydroxide solution, and a phase transfer catalyst, such as tetra-n-butylammonium hydroxide, may be advantageous for this purpose. In this case, the reaction is carried out, for example, at from 10° C. to the boiling point of one of the components of the solvent mixture. c) Stepwise reaction with a methylene halide and an alkali metal thiocyanate

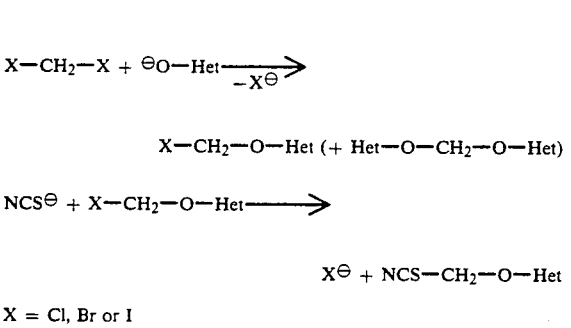

X = Cl, Br or I

The synthesis disclosed in U.S. Pat. No. 3,520,976 is carried out as a rule in an inert solvent, particularly preferably in acetone.

In the first reaction step, the alcoholate IIb is reacted with a methylene halide, preferably bromochloromethane, to give the halomethyl ether IV, an acetal V of formaldehyde being formed as a byproduct.

In order to keep the formation of the byproduct at as low a level as possible, it is advisable to use an excess of methylene halide III with respect to the alcoholate, i.e. up to about 10 times the amount.

In general, the reaction is carried out at about 20° C. (room temperature) or at slightly elevated temperature of up to about 40° C.

The reaction of the halomethyl ether IV (pure or contaminated with acetal V) with a thiocyanate, for example an alkali metal thiocyanate or, preferably, ammonium thiocyanate, is advantageously carried out using a stoichiometric ratio or using an excess of thiocyanate of up to about 25%.

A reaction temperature of from about −20° C. to the boiling point of the solvent is advantageously used.

Regarding the pressure, the statements made for method a) are applicable.

The 1-hydroxyhetero compounds of the formula IIa are known or can be prepared by known processes. Synthesis routes are described in, for example, the following publications:

for 1-hydroxypyrazoles: EP-A 347 676 and EP-A 347 689, for 1-hydroxyimidazoles: Synthesis, 773 (1989) and DE 39 32 552, for 1-hydroxy-1,2,3-triazole: Ber. 27 (1984), 3381, for 1-hydroxy-1,2,4-triazoles: DE 39 00 347, for 1-hydroxyindazoles: DE 25 22 314 and EP 347 676 and for 1-hydroxybenzimidazoles: Synthesis, 703 (1975) and DE 39 32 552.

1-Hydroxybenz-1,2,3-triazole is commercially available.

Suitable acid addition salts are the salts of acids which do not adversely affect the fungicidal action of I, for example the hydrochlorides, hydrobromides, sulfates, nitrates, phosphates, oxalates or dodecylbenzenesulfonates.

Suitable metal complexes are the complexes of copper, of zinc, of tin, of manganese, of iron, of cobalt or of nickel. The complexes are preferably prepared from the free bases I and salts of the metals with mineral acids, for example the chlorides or sulfates. Preparation Examples

EXAMPLE 1

3,5-Dimethyl-1-thiocyanatomethoxypyrazole

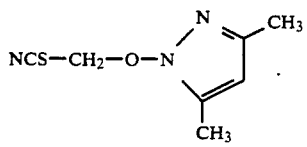

11.2 g 10.1 mol) of 50% strength aqueous potassium hydroxide solution and then about 15 g of a 3 Å molecular sieve were added to a solution of 11.2 g (0.1 mol) of 3,5-dimethyl-1-hydroxypyrazole in 350 ml of diethylene glycol dimethyl ether at about 20° C. 13.0 g (0.1 mol) of methylene bisthiocyanate were then stirred into the mixture. After the end of the addition, stirring was continued for a further 4 hours at room temperature (about 20° C.), after which the molecular sieve was filtered off and the filtrate was evaporated down. The residue was dissolved in diethyl ketone and the organic phase was washed with aqueous sodium bicarbonate solution, after which working up was carried out in a conventional manner to give the product in a yield of 51%.

The pale yellow solid was recrystallized from cyclohexane.

The physical data of the compound are shown in Table A, which lists further compounds I which were prepared in the same manner.

TABLE A

| | | NCS—CH$_2$—O—Het I | | |
|---|---|---|---|---|
| No. | Het | mp. [°C.] | $^1$H-NMR [ppm] | IR [cm$^{-1}$] |
| 1 | 3,5-Dimethyl-pyrazole | 65–70 | 2.10(s, 3H); 2.24(s, 3H); 5.89(s, 1H); 6.02(s, 2H); [in d$^6$-DMSO] | |
| 2 | 4-Methyl-pyrazole | Oil | 2.07(s, 3H); 5.73(s, 2H); 7.13(s, 1H); 7.29(s, 1H) [in CDCl$_3$] | 2160, 1280, 1130, 985, 638 |
| 2 | 1,2,3-Benztri-azole | Oil | 6.27(s, 2H); 7.48(m, 1H); 7.63(m, 1H); 7.79(m, 1H); 8.02(m, 1H) | 2160, 1085, 970 930, 910, 780, 730, 680 |

TABLE A-continued

| No. | Het | NCS—CH$_2$—O—Het I | | |
|---|---|---|---|---|
| | | mp. [°C.] | $^1$H-NMR [ppm] | IR [cm$^{-1}$] |
| 4 | 3-Methyl-pyrazole | Oil | [in CDCl$_3$ + d$^6$-DMSO] 2.02(s, 3H); 5.99(s, 3H); 7.18(s, 1H); 7.63(s, 1H) | 2160, 1277, 1125, 983, 945, 635 |
| 5 | 1,2,4-Triazole | Oil | [in d$^6$-DMSO] 6.11(s, 2H); 8.03(s, 1H); 8.82(s, 1H) | 2160, 1485, 1275, 1125, 1000, 945, 680, 610 |
| 6 | Benzimidazole | Oil | [in d$^6$-DMSO] | |
| 7 | Imidazole | Oil | | |

The novel active ingredients are particularly suitable for preventing various materials from being degraded or destroyed by bacteria or fungi or from being attacked and overgrown by microorganisms. Materials which can be preserved with the novel active ingredients or treated with a microcidal preparation of said ingredients are, for example, glues and adhesives, starch solutions, wax emulsions, clay emulsions, sizes, finishes, spinning baths, gelatine formulations, putty, joint sealing compounds, cooling lubricants, drilling oils, fuels, plastics dispersions, emulsion paints, textiles, leather, raw hides and cosmetics. The compounds are also suitable as slime control agents in the paper industry, in recooling systems and in air humidification systems.

The compounds I are also suitable for protecting the following plant species from attack by microorganisms: cereals (e.g. wheat, barley, rye, oats, rice, sorghum and related cereals), beets (e.g. sugar beet and fodder beet), pomes, drupes and berry fruit (e.g. apples, pears, plums, peaches, almonds, cherries, strawberries, raspberries and blackberries), legumes (e.g. beans, lentils, peas and soybean), oil crops (e.g. rape, mustard, poppy, olives, sunflowers, coconut, castor oil plant, cocoa and peanuts), cucurbitaceae (e.g. squash, cucumbers and melons), fiber plants (e.g. cotton, flax, hemp and jute), citrus fruits (e.g. oranges, lemons, grapefruits and mandarins), vegetable varieties (e.g. spinach, lettuce, asparagus, cabbage varieties, carrots, onions, tomatoes, potatoes and capsicum), lauraceae (e.g. avocado, cinnamon and camphor) or plants such as corn, tobacco, nuts, coffee, sugar cane, tea, grapevines, hops and banana and natural rubber plantations. For the purposes of the present invention, however, plants include all species of other green cultures, i.e. ornamentals (composites), grass areas, banks or general cover crops.

The following microorganisms can be controlled, for example, with the novel compounds I:

*Staphylococcus aureus, Escherichia coli, Klebsielle pneumoniae, Citrobacter freundii, Proteus vulgaris, Pseudomonas aeruginosa, Desulfovibrio desulfuricans, Streptoverticillium rubrireticuli, Aspergillus niger, Aspergillus versicolor, Penicillium funiculosum, Penicillium expansum, Penicillium glaucum, Paecilomyces variotii, Trichoderma viride, Chaetomium globosum, Aspergillus amstelodami, Phoma pigmentovora, Phoma violacea, Aureobasidium pullulans, Saccharomyces cerevisiae, Alternaria tenuis, Stemphylium macrosporoideum, Cladosporium herbarum, Cladosporium resinae, Candida albicans, Trichophyton mentagrophytes, Geotrichum candidans, Monilia sitophila, Scenedesmus quad-ricauda, Chlorella vulgaris, Nostoc muscorium, Oscillatoria limosa and Anabaena constricta.*

The novel substances can be converted into the conventional formulations, such as solutions, emulsions, suspensions, dusts, powders, pastes and granules. The application forms depend entirely on the intended uses; they should in any case ensure fine and uniform distribution of the active substances. The formulations are prepared in a known manner, for example by extending the active ingredient with solvents and/or carriers, with or without the use of emulsifiers and dispersants; where water is used as a diluent, other organic solvents may also be used as auxiliary solvents. Assistants which are suitable for this purpose are essentially solvents, such as aromatics (e.g. xylene or benzene), chlorinated aromatics (e.g. chlorobenzenes), paraffins (e.g. mineral oil fractions), alcohols (e.g. methanol or butanol), amines (e.g. ethanolamine or dimethylformamide) and water, carriers such as ground natural minerals, e.g. kaolins, aluminas, talc or chalk, and ground synthetic minerals (e.g. finely divided silica or silicates), emulsifiers, such as nonionic and anionic emulsifiers (e.g. polyoxyethylene fatty alcohol ethers, alkylsulfonates and arylsulfonates), and dispersants, such as ligninsulfite waste liquors and methylcellulose.

The formulations contain in general from 0.1 to 95, preferably from 0.5 to 90, % by weight of active ingredient. The active ingredients are used in a purity of from 90 to 100%, preferably from 95 to 100%.

The application concentration usually chosen is from 0.001 to 5, preferably from 0.01 to 2, % by weight, based on the weight of the material to be protected, of active ingredient; when used for the treatment of water, in oil production, in drilling and cutting oils, in fuels, in swimming pools, in recooling systems, in air humidification systems or in the paper industry, amounts of active ingredient of from 5 to 500 ppm are sufficient. Ready-to-use disinfectant solutions contain, for example, from 0.5 to 10% by weight of active ingredient.

Examples of suitable formulations are:

I. A solution of 90 parts by weight of compound No 1 and 10 parts by weight of N-methyl-α-pyrrolidone, which is suitable for use in the form of very small drops.

II. A mixture of 20 parts by weight of compound No. 2, 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By finely distributing the mixture in 100,000 parts by weight of water, a dispersion which contains 0.02% by weight of active ingredient is obtained.

III. An aqueous dispersion of 20 parts by weight of compound No. 3, 40 parts by weight of cyclohexanone, 30 parts by weight of isobutanol and 20 parts by weight of the adduct of 40 moles of ethylene oxide with 1 mole of castor oil. A mixture of this dispersion with 100,000 parts by weight of water contains 0.02% by weight of the active ingredient.

IV. An aqueous dispersion of 20 parts by weight of compound No. 4, 25 parts by weight of cyclohexanol, 65 parts by weight of a mineral oil fraction boiling within a range from 210° to 280° C. and 10 parts by weight of the adduct of 40 moles of ethylene oxide with 1 mole of castor oil. A mixture of this dispersion with 100,000 parts by weight of water contains 0.02% by weight of the active ingredient.

V. A mixture milled in a hammer mill and consisting of 80 parts by weight of compound No. 5, 3 parts by weight of the sodium salt of diisobutylnaphthalene-α-sulfonic acid, 10 parts by weight of the sodium salt of a ligninsulfonic acid obtained from a sulfite waste liquor and 7 parts by weight of a silica gel powder. By finely distributing the mixture in 20,000 parts by weight of water, a spray liquor which contains 0.1% by weight of the active ingredient is obtained.

VI. An intimate mixture of 3 parts by weight of compound No. 6 and 97 parts by weight of finely divided kaolin. This dusting agent contains 3% by weight of active ingredient.

VII. An intimate mixture of 30 parts by weight of compound No. 7, 92 parts by weight of silica gel powder and 8 parts by weight of liquid paraffin which has been sprayed onto the surface of the silica gel. This formulation imparts good adhesion to the active ingredient.

VIII. A stable aqueous dispersion of 40 parts by weight of compound No. 1, 10 parts by weight of the sodium salt of a phenolsulfonicacid/urea/formaldehyde condensate, 2 parts by weight of silica gel and 48 parts by weight of water, which can be further diluted.

IX. A stable oily dispersion of 20 parts by weight of compound No. 2, 2 parts by weight of the calcium salt of dodecylbenzenesulfonic acid, 8 parts by weight of a fatty alcohol polyglycol ether, 20 parts by weight of the sodium salt of a phenolsulfonic acid-/urea/formaldehyde condensate and 68 parts by weight of a paraffinic mineral oil.

X. A mixture milled in a hammer mill and consisting of 10 parts by weight of compound No. 5, 4 parts by weight of the sodium salt of diisobutyl-naphthalene-α-sulfonic acid, 20 parts by weight of the sodium salt of a ligninsulfonic acid obtained from a sulfite waste liquor, 38 parts by weight of silica gel and 38 parts by weight of kaolin. By finely distributing the mixture in 10,000 parts by weight of water, a spray liquor which contains 0.1% by weight of the active ingredient is obtained.

The active ingredients alone act as low-foam biocides. A substantial increase in the action of biocidal formulations containing these compounds is achieved if tri-$C_6$-$C_{12}$-alkylmethylammoniuxsalts are added to them, preferably in amounts of from 20 to 40% by weight, based on the weight of the compounds of the general formula I.

The active ingredients can also be mixed with other known microbicides. In many cases, a synergistic effect is obtained, i.e. the microbicidal activity of the mixture is greater than the (summed) activities of the individual components.

The known microbicides can be mixed with the novel substances in a weight ratio of from 1:100 to 100:1.

USE EXAMPLE

The comparative substance used was 1-thiocyanatomethoxypyrazole methoxypyrazole

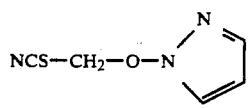

disclosed in EP-A 0 249 977 (compound No. 6).

Active ingredient 1, dissolved in propylene glycol, was added in amounts of 0.1, 0.05, 0.025, 0.01, 0.005, 0.0025 and 0.001%, based on the weight of the dispersion, to an aqueous dispersion which was highly susceptible to microorganisms and was based on polyacrylate. Thereafter, 100 ml portions of the test batches were inoculated with a microorganism suspension which contained, as microorganisms, Staphylococcus aureus, Escherichia coli, Pseudomonas aeruginosa, Proteus mirabilis, Aspergillus niger, Penicillium funiculosum, Cladosporium verbarum, Alternaria teunis, Geotrichum candidans, Candida lypolitica and Pichia bispora. The microorganism density in the inoculated dispersion was from $10^6$ to $10^7$ microorganisms/ml. After an incubation time of 21 days at 25° C., the samples were transferred from the test batches to agar nutrient media suitable for the growth of bacteria, mold and yeast fungi and were incubated for 3 and 7 days in order to detect still viable microorganisms.

The result showed that as little as 0.0025% of active ingredient 1 is sufficient to preserve an aqueous polyacrylate dispersion from attack by microorganisms. In contrast, 0.05% of the comparative active ingredient was required in order to obtain the same effect.

We claim:

1. An N-thiocyanatomethoxyazaheterocycle of the formula I

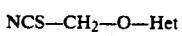

where Het is pyrazole-1-yl which carries on a carbon atom two $C_1$-$C_4$-alkyl groups or phenyl which may be monosubstituted to trisubstituted by halogen, $C_1$-$C_4$-alkyl or $C_1$-$C_4$-alkoxy or partially or completely halogenated $C_1$-$C_4$-alkyl, or the plant-tolerated salts or metal complexes thereof.

2. A biocide composition containing a biocidal amount of an N-thiocyanatomethoxyazaheterocycle of the formula I, its plant-tolerated salts or metal complexes as claimed in claim 1, and a liquid or solid carrier admixed therewith.

3. A method of controlling microorganisms, wherein a biocidal amount of an N-thiocyanatomethoxyazaheterocycle of the formula I or of its plant-tolerated salts or metal complexes as claimed in claim 1 is allowed to act on the microorganisms or on the articles, liquids or suspensions threatened by attack by microorganisms.

* * * * *